United States Patent
Qing et al.

(10) Patent No.: US 11,907,523 B2
(45) Date of Patent: Feb. 20, 2024

(54) METHOD FOR RESPONDING TO OPERATION TRAJECTORY AND MONITOR

(71) Applicant: SHENZHEN MINDRAY BIO-MEDICAL ELECTRONICS CO., LTD., Shenzhen (CN)

(72) Inventors: Lei Qing, Shenzhen (CN); Shuaijun Liu, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 478 days.

(21) Appl. No.: 16/805,416

(22) Filed: Feb. 28, 2020

(65) Prior Publication Data
US 2020/0201539 A1 Jun. 25, 2020

Related U.S. Application Data

(63) Continuation of application No. PCT/CN2017/099621, filed on Aug. 30, 2017.

(51) Int. Cl.
*G06F 3/0488* (2022.01)
*G16H 10/60* (2018.01)
(Continued)

(52) U.S. Cl.
CPC ...... *G06F 3/04883* (2013.01); *G06F 3/04842* (2013.01); *G06F 3/04886* (2013.01); *G16H 10/60* (2018.01); *G06F 2203/04104* (2013.01)

(58) Field of Classification Search
None
See application file for complete search history.

(56) References Cited

U.S. PATENT DOCUMENTS

2011/0221590 A1  9/2011  Baker et al.
2013/0297344 A1* 11/2013 Cosentino ........ A61N 1/37211
                                                705/3
(Continued)

FOREIGN PATENT DOCUMENTS

CN    101152077 A    4/2008
CN    101606159 A   12/2009
(Continued)

OTHER PUBLICATIONS

First Office Action issued in related Chinese Application No. 201780094459.4, dated Oct. 12, 2023, 32 pages.
(Continued)

*Primary Examiner* — Krishna P Neupane
(74) *Attorney, Agent, or Firm* — BAYES PLLC

(57) ABSTRACT

A method for responding to an operation trajectory is disclosed. The method is applied to a monitor configured to monitor and display physiological data of a patient. The method includes displaying at least one physiological data of a first patient on a display interface. The at least one physiological data comprises at least one of electrocardiogram, blood oxygen, blood pressure, respiration rate, body temperature and heart rate. The method further includes detecting a screen-touching operation triggered by a user on the display interface and acquiring an operation trajectory corresponding to the screen-touching operation according to the screen-touching operation. The operation trajectory includes a start point and an end point, the start point corresponding to a first time point, the end point corresponding to a second time point, and the second time point being later than the first time point. The method also includes if the screen-touching operation satisfies a pre-set operation trajectory, executing a patient release operation on the first patient at the second time point.

23 Claims, 8 Drawing Sheets

(51) Int. Cl.
    *G06F 3/04883* (2022.01)
    *G06F 3/04842* (2022.01)
    *G06F 3/04886* (2022.01)

(56) References Cited

U.S. PATENT DOCUMENTS

| | | |
|---|---|---|
| 2014/0278523 A1 | 9/2014 | Vaglio |
| 2017/0021184 A1* | 1/2017 | Pavel ........................ A61B 7/02 |
| 2017/0188979 A1* | 7/2017 | Volpe ...................... A61B 5/349 |
| 2018/0114601 A1* | 4/2018 | Ou ........................ G16H 40/67 |

FOREIGN PATENT DOCUMENTS

| | | |
|---|---|---|
| CN | 101751506 A | 6/2010 |
| CN | 104750406 A | 7/2015 |
| CN | 104750407 A | 7/2015 |
| CN | 105512506 A | 4/2016 |

OTHER PUBLICATIONS

"Philips Monitor MP20 Instruction", Samsungcap, http://www.docin.com/p-690304610.html, Aug. 16, 2013, pp. 1, 13-14, 79-85.
Philips. IntelliVue, "IntelliVue Patient Monitor Instruction", http://www.docin.com/p-1685833727.html, Jul. 23, 2016, 3 pages.
International Search Report in corresponding International Application No. PCT/CN2017/099621, dated May 25, 2018, 6 pages.
First Office Action issued in related Chinese Application No. 201780094459.4, dated Mar. 15, 2023, 23 pages.

\* cited by examiner

METHOD FOR RESPONDING TO OPERATION TRAJECTORY AND MONITOR

CROSS-REFERENCE TO RELATED APPLICATIONS

This application is a bypass continuation of PCT Application No. PCT/CN2017/099621, filed Aug. 30, 2017, which is incorporated herein by reference.

TECHNICAL FIELD

The present disclosure relates to the field of interface interaction, and in particular to a method for responding to an operation trajectory and a monitor.

BACKGROUND

A monitor can synchronously and continuously monitor a patient's electrocardiogram, blood pressure, respiration, body temperature, and other parameters, and provides an effective approach for medical personnel to comprehensively and intuitively know the patient's conditions in time. With the gradual modernization of hospitals, more monitors will be clinically used and become the most commonly used medical devices in wards.

In some cases, a patient needs to be transferred, and an emergency transfer monitor is needed at this time. Such monitors are usually small in size, which facilitates portability. When the patient does not need to be monitored with the monitor, the patient's physiological data can be released by operating the monitor, and the monitor is restored to a default configuration to facilitate monitoring of a next patient.

However, such a portable monitor is small and accordingly has a small screen due to the small volume, so that it is usually necessary to click on menu buttons on the screen many times when the physiological data is release, and there are many menu layers. Therefore, the small screen is not easy to operate, thus reducing the ease of use of the monitor.

SUMMARY

Embodiments of the present disclosure provide a method for responding to an operation trajectory and a monitor. On a smaller screen of a monitor, release of physiological data can be completed through an operation trajectory without needing to click on a menu button on a small screen multiple times, which is convenient for a user to operate and improves the ease of use of a monitor.

In view of this, a first aspect of embodiments of the present disclosure provides a method for responding to an operation trajectory, the method being applied to a monitor configured to monitor and display physiological data of a patient, the method comprising:

displaying at least one piece of physiological data of a first patient on a display interface, wherein the at least one physiological data comprises at least one of electrocardiogram, blood oxygen, blood pressure, respiration rate, body temperature and heart rate;
detecting a screen-touching operation triggered by a user on the display interface;
acquiring an operation trajectory corresponding to the screen-touching operation according to the screen-touching operation, wherein the operation trajectory includes a start point and an end point, the start point corresponds to a first time point, the end point corresponds to a second time point, and the second time point is later than the first time point; and
if the screen-touching operation satisfies a pre-set operation trajectory, executing a patient release operation on the first patient at the second time point.

A second aspect of embodiments of the present disclosure provides an operation trajectory response device, wherein the operation trajectory response device is applied to a monitor, the monitor is configured to monitor and display physiological data of a patient, and the operation trajectory response device comprises:

a display module configured to display at least one physiological data of a first patient on a display interface, wherein the at least one physiological data comprises at least one of electrocardiogram, blood oxygen, blood pressure, respiration rate, body temperature and heart rate;
a detection module configured to detect a screen-touching operation triggered by a user on the display interface;
an acquisition module configured to acquire an operation trajectory corresponding to the screen-touching operation according to the screen-touching operation detected by the detection module, wherein the operation trajectory includes a start point and an end point, the start point corresponds to a first time point, the end point corresponds to a second time point, and the second time point is later than the first time point; and
a processing module configured to, if the screen-touching operation acquired by the acquisition module satisfies a pre-set operation trajectory, execute a patient release operation on the first patient at the second time point.

A third aspect of embodiments of the present disclosure provides a monitor, comprising a touch display screen, a processor, a memory, at least one physiological data monitoring module and a bus system, wherein the at least one physiological data monitoring module is configured to monitor at least one physiological data of a patient;
the memory is configured to store a program, an instruction, and the at least one physiological data of the patient;
the touch display screen receives the screen-touching operation under the control of the processor;
the processor is configured to execute the program in the memory;
the processor is configured to execute the program in the memory;
the bus system is configured to be connected to the memory, the at least one physiological data monitoring module and the processor to enable the memory and the processor to perform communication; and
the processor is configured to perform the following steps:
displaying at least one physiological data of a first patient on a display interface of the touch display screen, wherein the at least one physiological data comprises at least one of electrocardiogram, blood oxygen, blood pressure, respiration rate, body temperature and heart rate;
detecting a screen-touching operation triggered by a user on the display interface;
acquiring an operation trajectory corresponding to the screen-touching operation according to the screen-touching operation, wherein the operation trajectory includes a start point and an end point, the start point corresponds to a first time point, the end point corresponds to a second time point, and the second time point is later than the first time point; and if the screen-touching operation satisfies a pre-set operation trajectory, executing a patient release operation on the first patient at the second time point.

A fourth aspect of embodiments of the present disclosure provides a computer program product comprising an instruction, wherein when the instruction is executed on a computer, the computer performs the method provided in the first aspect.

A fifth aspect of embodiments of the present disclosure provides a computer-readable storage medium comprising an instruction, wherein when the instruction is executed on a computer, the computer performs the method provided in the first aspect.

DETAILED DESCRIPTION OF EMBODIMENTS

Embodiments of the present disclosure provide a method for responding to an operation trajectory and a monitor. On a smaller screen of a monitor, release of physiological data can be completed through an operation trajectory without needing to click on a menu button on a small screen multiple times, which is convenient for a user to operate and improves the ease of use of a monitor.

The terms "first", "second", "third", "fourth", etc. (if any) in the specification and the claims of the present disclosure and the above-mentioned drawings are used to distinguish similar objects and are not necessarily used to describe a specific order or sequence. It should be understood that the terms used as such is interchangeable where appropriate, so that the embodiments of the present disclosure described herein can be implemented in an order other than what is illustrated or described herein. Moreover, the terms "comprise" and "have" or any variation of such terms are intended to cover a non-exclusive inclusion. For example, a process, method, system, product or device that comprises a series of steps or units not only includes those steps or units specified expressly, but also includes other steps or units that are not specified expressly or are inherent to the process, method, product or device.

Figure 1:
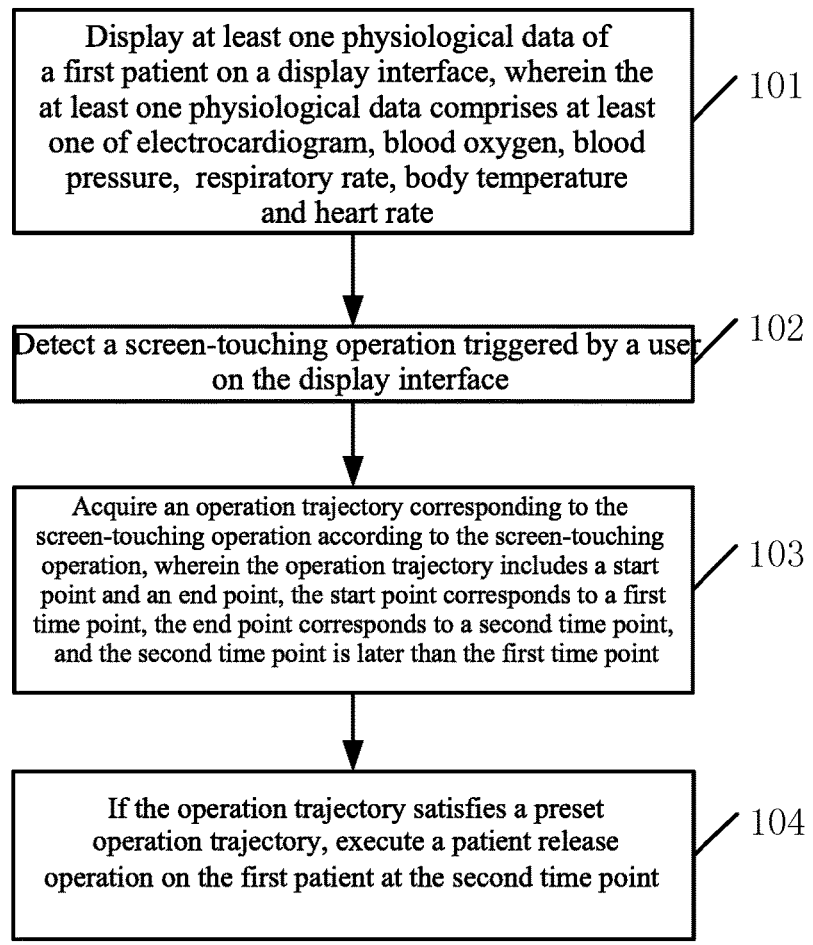
FIG. 1 is a schematic diagram of one embodiment of a method for responding to an operation trajectory according to embodiments of the present disclosure.

A method for responding to an operation trajectory in the present disclosure is described below in detail. Referring to FIG. 1, an embodiment of the present disclosure provides a method for responding to an operation trajectory. The method is applied to the monitor, is particularly applicable to a monitor comprising a touch display screen, and is used to contact the touch display screen to input a screen-touching operation. The monitor is configured to monitor physiological data of at least one patient. The embodiment of the method for responding to an operation trajectory includes the following steps:

101. At least one physiological data of a first patient is displayed on a display interface, wherein the at least one physiological data comprises at least one of electrocardiogram, blood oxygen, blood pressure, respiration rate, body temperature, and heart rate. For example, the physiological data is displayed on a touch display screen.

In this embodiment, the at least one physiological data of the first patient may be displayed on the display interface of the monitor. The at least one physiological data may comprise, but is not limited to, at least one of electrocardiogram, heart rate, respiration, invasive blood pressure, non-invasive blood pressure, cardiac output, body temperature, and blood gas.

Electrocardiography is one of the most basic monitoring projects of a monitoring instrument, and an electrocardiographic signal is obtained through electrodes. Heart rate is the number of beats of the heart per minute. In heart rate measurement, an instantaneous heart rate and an average heart rate are measured according to an electrocardiographic waveform. Generally, a heart rate alarm range of the monitor comprises a low limit of 20 beats/min to 100 beats/min and a high limit of 80 beats/min to 240 beats/min. For the respiration, a patient's respiratory frequency, that is, respiration rate, is monitored. Respiratory frequency is the number of breaths within a unit of time of a patient, and the unit is minute. A patient's invasive blood pressure, central venous pressure, left atrial pressure, cardiac output, and cardiac floating catheter are monitored. For the non-invasive blood pressure, Korotkoff sounds are detected for monitoring. An inflatable cuff is used to block brachial artery. A series of sounds with different tones appear as blocking pressure decreases. Systolic pressure and diastolic pressure may be determined according to the tones and time. Cardiac output is an important indicator for assessing the cardiac function. In some pathological conditions, cardiac output decreases, leading to insufficient nutritional supply to the body. Cardiac output is the volume of blood ejected by the heart per minute. To measure cardiac output, a particular amount of indicator is injected into the blood in a manner. The indicator diffuses in the blood, and a change of the indicator is measured to calculate cardiac output. Body temperature reflects a metabolic result of an organism and is one of the conditions that ensure normal functions and activities of the organism. Pulse is a phenomenon that an arterial blood vessel pulsates rhythmically as the heart expands and contracts. Pulse comprises changes of a plurality of physical quantities such as intravascular pressure, volume, displacement, and blood vessel wall tension. Blood gas monitoring mainly comprises partial pressure of oxygen, partial pressure of carbon dioxide, and oxyhemoglobin saturation.

102. A screen-touching operation triggered by a user on the current display interface is detected.

In this embodiment, the screen-touching operation input by the user may be detected while the monitor detects the physiological data of the first patient or after the monitor completes monitoring of the physiological data of the first patient. For example, the completing monitoring of the physiological data of a patient may be pulling out connected sensor components configured to detect the physiological data of the patient from the patient's body. In one of the embodiments, as the monitor monitors the physiological data of the first patient, the screen-touching operation triggered by the user on the current display interface of the monitor may be detected in real time. The first patient is an object that is currently monitored by the monitor and may usually be a patient.

In this embodiment, the current display interface of the monitor may be configured to display the at least one physiological data of the first patient. The at least one physiological data comprises at least one of electrocardiogram, blood oxygen, blood pressure, respiration rate, body temperature, heart rate, etc.

103. An operation trajectory corresponding to the screen-touching operation is acquired according to the screen-touching operation, wherein the operation trajectory includes a start point and an end point, the start point corresponds to a first time point, the end point corresponds to a second time point, and the second time point is later than the first time point.

In this embodiment, the monitor may acquire the operation trajectory corresponding to the screen-touching operation according to the screen-touching operation of the user. The operation trajectory is a distance by which the user uses a finger to keep moving on the display interface of the monitor. Therefore, a valid operation trajectory includes a start point and an end point, and the start point and the end point do not overlap. The start point corresponds to a first time point, the end point corresponds to a second time point, the first time point is the time point at which the finger is placed on the display interface of the monitor, the second time point is the time point at which the finger leaves the display interface of the monitor, and the second time point is later than the first time point.

104. If the operation trajectory satisfies a pre-set operation trajectory, a patient release operation on the first patient is executed at the second time point.

In this embodiment, if the monitor determines that the operation trajectory triggered by the user satisfies the pre-set operation trajectory, the monitor executes the patient release operation on the first patient at the second time point. The patient release operation may eliminate a binding relationship between the monitor and a patient, so that the monitor can monitor another patient. Generally, one monitor is bound to one patient. After the binding, the monitor can only process in real time a sensor signal transmitted from the body of a current bound patient and display the sensor signal on the current display interface. Therefore, after the patient release operation, the monitor can monitor in real time physiological data obtained from a second patient other than the first patient and display the physiological data on the current display interface of the second patient.

An embodiment of the present disclosure provides a method for responding to an operation trajectory. The method is applied to the monitor. The monitor is configured to monitor and display at least one physiological data of a patient. First, a screen-touching operation triggered by a user on the current display interface is detected. The monitor may then acquire an operation trajectory corresponding to the screen-touching operation according to the screen-touching operation. The operation trajectory includes a start point and an end point. The start point corresponds to a first time point, the end point corresponds to a second time point, and the second time point is later than the first time point. If the operation trajectory satisfies the pre-set operation trajectory, the monitor executes a patient release operation on the first patient at the second time point. In the above manner, on a smaller screen of a monitor, release of physiological data can be completed through an operation trajectory without needing to click on a menu button on a small screen multiple times, which is convenient for a user to operate and improves the ease of use of a monitor.

In some embodiments, based on the foregoing embodiment corresponding to FIG. 1, in a first optional embodiment of the method for responding to an operation trajectory provided in the embodiment of the present disclosure, after the acquiring an operation trajectory corresponding to the screen-touching operation according to the screen-touching operation, the method may further comprise:

determining whether the operation trajectory is a swipe trajectory, wherein the direction of the swipe trajectory is at least one of up, down, left, and right; and if the operation trajectory is the swipe trajectory, confirming that the operation trajectory satisfies the pre-set operation trajectory.

In this embodiment, a first pre-set operation trajectory, that is, a swipe trajectory, is described. The monitor determines whether the operation trajectory triggered by the user is a swipe trajectory, and if yes, confirms that the operation trajectory of the user satisfies the pre-set operation trajectory.

Figure 2A:
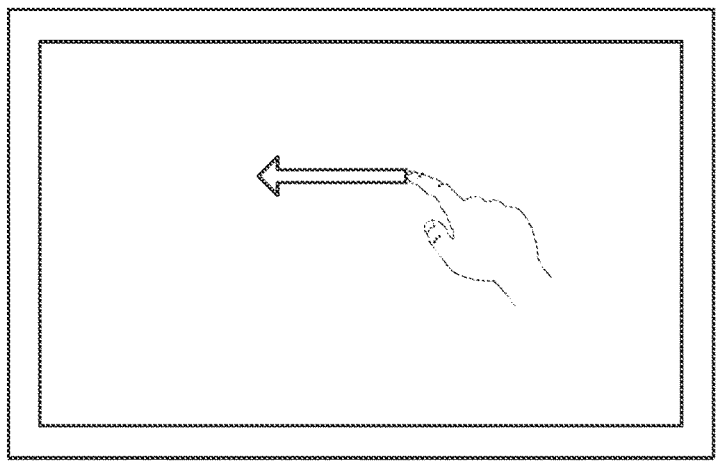
FIG. 2(a) is a schematic diagram of one embodiment of a swipe trajectory according to embodiments of the present disclosure.
Figure 2B:
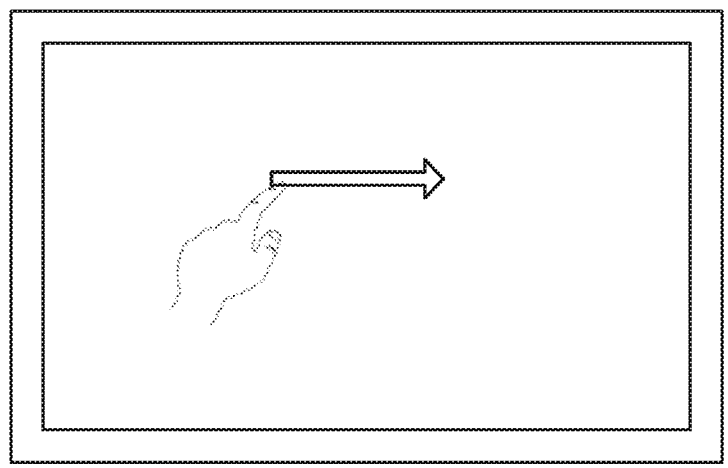
FIG. 2(b) is a schematic diagram of another embodiment of a swipe trajectory according to embodiments of the present disclosure.
Figure 2C:
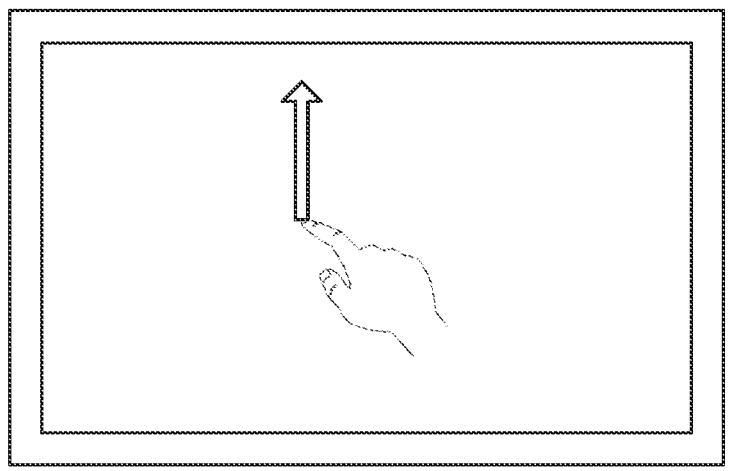
FIG. 2(c) is a schematic diagram of another embodiment of a swipe trajectory according to embodiments of the present disclosure.
Figure 2D:
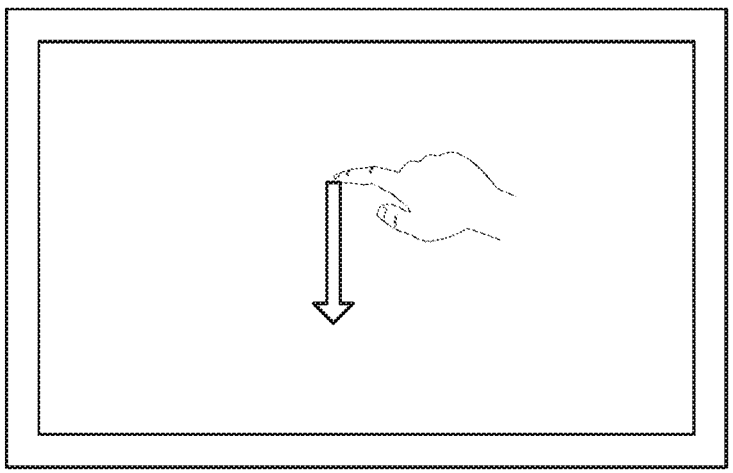
FIG. 2(d) is a schematic diagram of another embodiment of a swipe trajectory according to embodiments of the present disclosure.
Figure 2E:
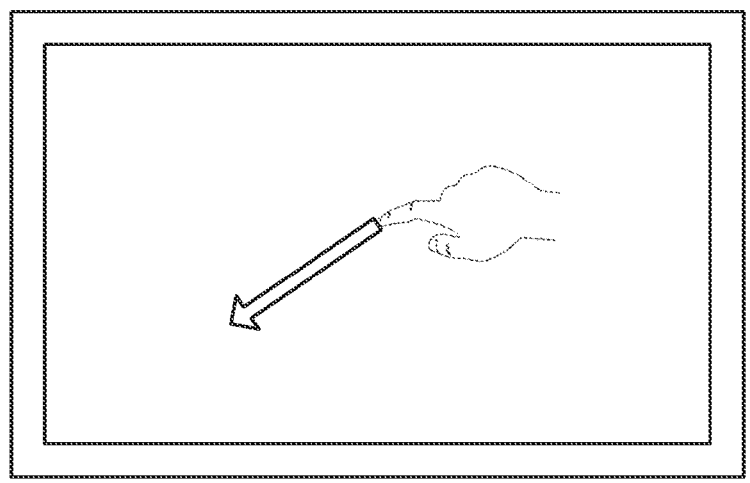
FIG. 2(e) is a schematic diagram of another embodiment of a swipe trajectory according to embodiments of the present disclosure.
Figure 2F:
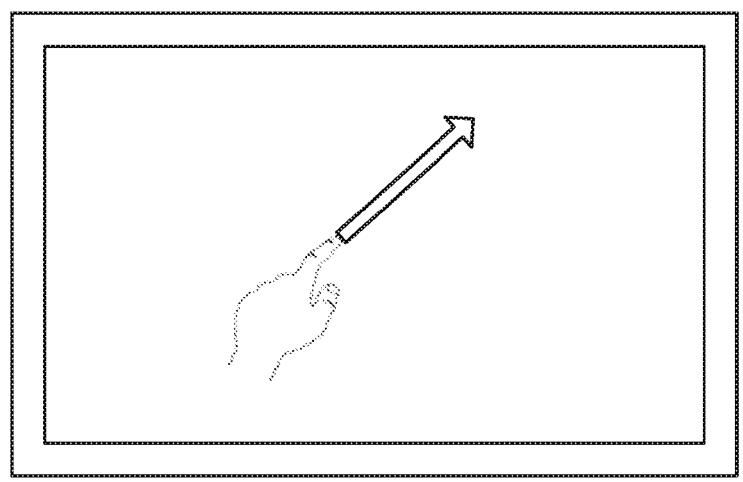
FIG. 2(f) is a schematic diagram of another embodiment of a swipe trajectory according to embodiments of the present disclosure.

For ease of introduction, referring to FIG. 2(a) to FIG. 2(f), FIG. 2(a) indicates that the swipe trajectory is a swipe from right to left, FIG. 2(b) indicates that the swipe trajectory is a swipe from left to right, FIG. 2(c) indicates that the swipe trajectory is a swipe from bottom to top, FIG. 2(d) indicates that the swipe trajectory is a swipe from top to bottom, FIG. 2(e) indicates that the swipe trajectory is a swipe from upper right to lower left, and FIG. 2(f) indicates that the swipe trajectory is a swipe from lower left to upper right.

It should be noted that various cases shown in FIG. 2(a) to FIG. 2(f) are merely schematics of the swipe trajectory. During actual application, the direction of the swipe trajectory is not limited to the foregoing cases. It may be understood that the pre-set operation trajectory may be one or more swipe trajectories. The patient release operation on the first patient can be executed provided that one swipe trajectory is satisfied.

Next, in this embodiment of the present disclosure, a finger may swipe on the display interface of the monitor to generate one swipe trajectory, and the swipe direction of the swipe trajectory is at least one of up, down, left, and right. In the foregoing manner, the pre-set operation trajectory is set as the swipe trajectory. The user only needs to execute a simple gesture operation to execute the patient release operation on the first patient, so that the monitor can be more conveniently used.

In some embodiments, based on the foregoing embodiment corresponding to FIG. 1, in a second optional embodiment of the method for responding to an operation trajectory provided in the embodiment of the present disclosure, after the acquiring an operation trajectory corresponding to the screen-touching operation according to the screen-touching operation, the method may further comprise:
  determining whether the operation trajectory is an arc trajectory, wherein the direction of the arc trajectory is clockwise or counterclockwise; and
  if the operation trajectory is an arc trajectory, confirming that the operation trajectory satisfies the pre-set operation trajectory.

In this embodiment, a second pre-set operation trajectory, that is, an arc trajectory, is described. The monitor determines whether the operation trajectory triggered by the user is an arc trajectory, and if yes, confirms that the operation trajectory of the user satisfies the pre-set operation trajectory.

Figure 3A:
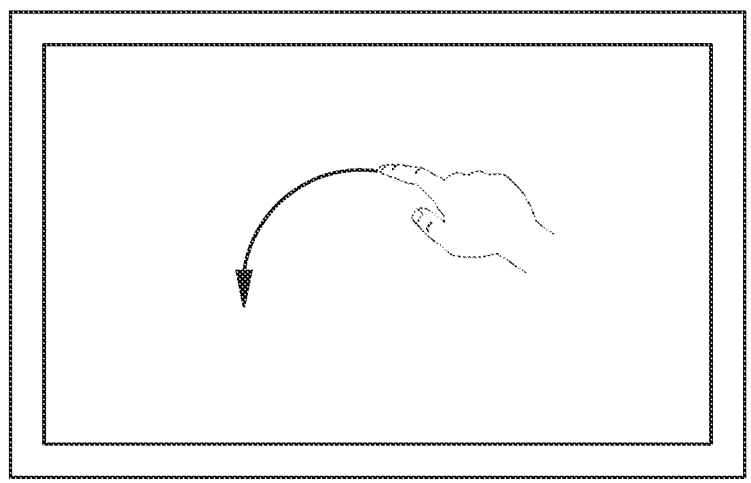
FIG. 3(a) is a schematic diagram of one embodiment of an arc trajectory according to embodiments of the present disclosure.
Figure 3B:
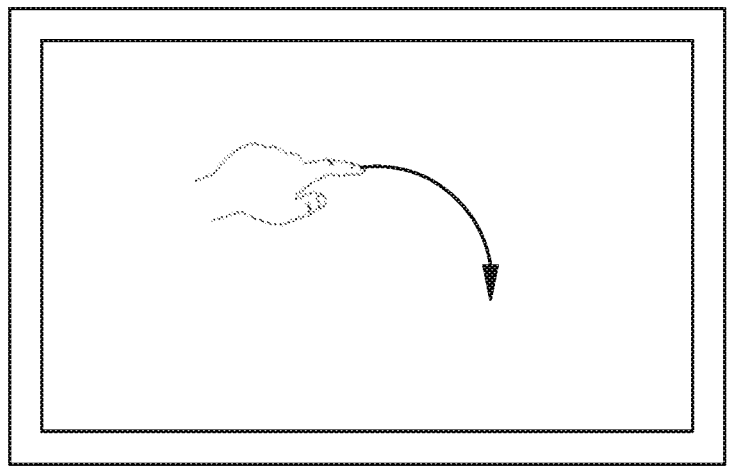
FIG. 3(b) is a schematic diagram of another embodiment of an arc trajectory according to embodiments of the present disclosure.

For ease of introduction, referring to FIG. 3(a) and FIG. 3(b), FIG. 3(a) indicates that a finger swipes counterclockwise on the display interface of the monitor, and FIG. 3(b) indicates that a finger swipes clockwise on the display interface of the monitor.

It should be noted that the cases shown in FIG. 3(a) and FIG. 3(b) are merely schematics of an arc trajectory. During actual application, the arc trajectory may be helical, inner spiral or outer spiral. It may be understood that the pre-set operation trajectory may be one or more arc trajectories. The patient release operation on the first patient can be executed provided that one arc trajectory is satisfied.

Next, in this embodiment of the present disclosure, a finger may swipe on the display interface of the monitor to generate one arc trajectory, and the swipe direction of the arc trajectory is clockwise or counterclockwise. In the foregoing manner, the pre-set operation trajectory is set as an arc trajectory. The user only needs to execute a simple gesture operation to execute the patient release operation on the first patient, so that the monitor can be more conveniently used.

In some embodiments, based on the foregoing embodiment corresponding to FIG. 1, in a third optional embodiment of the method for responding to an operation trajectory provided in the embodiment of the present disclosure, after the acquiring an operation trajectory corresponding to the screen-touching operation according to the screen-touching operation, the method may further comprise:
  determining whether the operation trajectory is a pre-set figure, wherein the pre-set figure is a closed figure or a non-closed figure; and
  if the operation trajectory is the pre-set figure, confirming that the operation trajectory satisfies the pre-set operation trajectory.

In this embodiment, a third pre-set operation trajectory, that is, the pre-set figure, is described. The monitor determines whether the operation trajectory triggered by the user is a pre-set figure, and if yes, confirms that the operation trajectory of the user satisfies the pre-set operation trajectory.

Figure 4A:
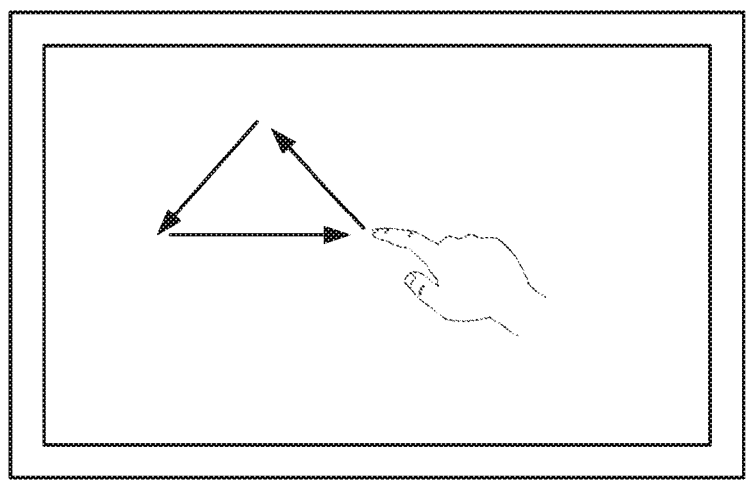
FIG. 4(a) is a schematic diagram of one embodiment of a pre-set figure according to embodiments of the present disclosure.
Figure 4B:
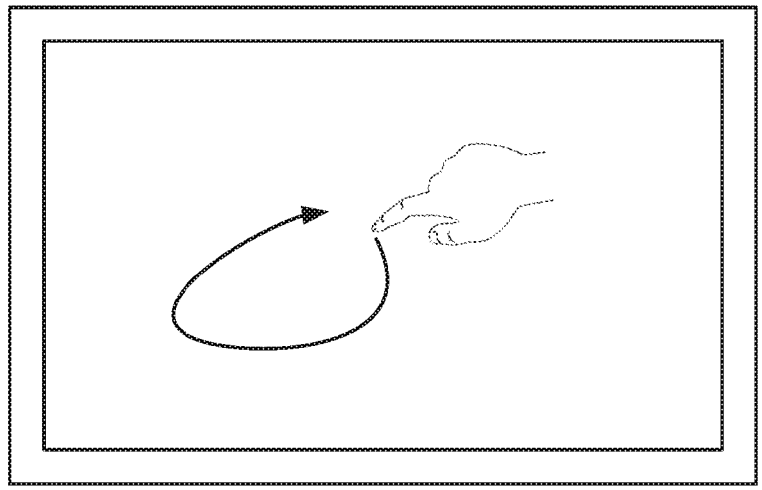
FIG. 4(b) is a schematic diagram of one embodiment of a pre-set figure according to embodiments of the present disclosure.

For ease of introduction, referring to FIG. 4(a) and FIG. 4(b), FIG. 4(a) indicates that a figure of a finger swiping on the display interface of the monitor, and the figure is a closed triangular figure. FIG. 4(b) indicates that a figure of a finger swiping on the display interface of the monitor, and the figure is a non-closed curve figure.

It should be noted that the cases shown in FIG. 4(a) and FIG. 4(b) are merely schematics of the pre-set figure. During actual application, the pre-set figure may be circular, rectangular, pentangular or the like. It may be understood that the pre-set operation trajectory may be one or more pre-set figures. The patient release operation on the first patient can be executed provided that one pre-set figure is satisfied.

Next, in this embodiment of the present disclosure, a finger may swipe on the display interface of the monitor to generate one pre-set figure, and the pre-set figure is a closed figure or a non-closed figure. In the foregoing manner, the pre-set operation trajectory is set as the pre-set figure. The user only needs to execute a simple gesture operation to execute the patient release operation on the first patient, so that the monitor can be more conveniently used, and the pre-set operation trajectory is more flexible.

In some embodiments, based on the foregoing embodiment corresponding to FIG. 1, in a fourth optional embodiment of the method for responding to an operation trajectory provided in the embodiment of the present disclosure, the screen-touching operation is triggered by one finger, or is triggered by two fingers, or is triggered by more than two fingers.

Figure 5A:
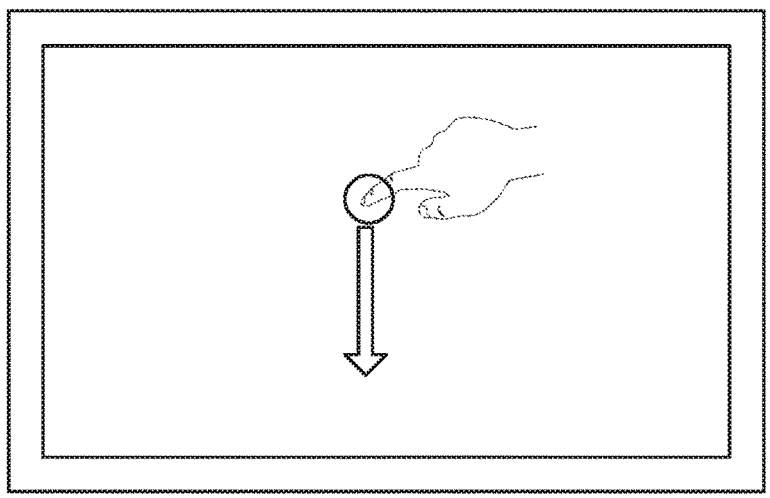
FIG. 5(a) is a schematic diagram of one embodiment of a screen-touching operation according to embodiments of the present disclosure.
Figure 5B:
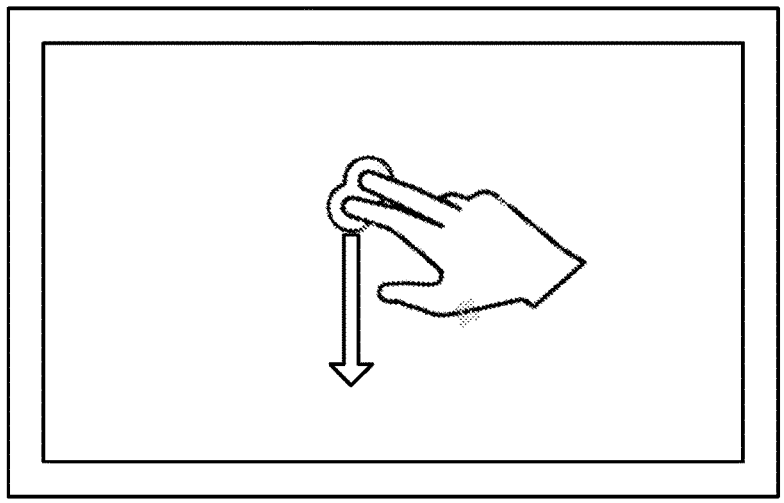
FIG. 5(b) is a schematic diagram of one embodiment of a screen-touching operation according to embodiments of the present disclosure.

In this embodiment, the user may further use at least one finger to complete the screen-touching operation. For ease of understanding, referring to FIG. 5(a), FIG. 5(a) is a schematic diagram of one embodiment of a screen-touching operation according to embodiments of the present disclosure. As shown in the figure, in this case, for example, the user uses one finger to execute an operation. Similarly, referring to FIG. 5(b), FIG. 5(b) is a schematic diagram of one embodiment of a screen-touching operation according to embodiments of the present disclosure. As shown in the figure, in this case, for example, the user uses two fingers to execute an operation.

It should be noted that during actual application, the user may use three fingers or more than three fingers to execute the screen-touching operation. This is not limited herein.

Next, in this embodiment of the present disclosure, when the user uses a finger to execute an operation on the display interface of the monitor, a quantity of fingers touching the display interface is not limited, so that operations are more flexible and feasible.

In some embodiments, based on any one of FIG. 1 and the foregoing first to fourth embodiments corresponding to FIG. 1, in a fifth optional embodiment of the method for responding to an operation trajectory provided in the embodiment of the present disclosure, the executing a patient release operation on the first patient at the second time point may comprise:

clearing physiological data of the first patient at the second time point; and establishing a data file of a second patient, wherein the data file is used to record physiological data of the second patient, and the second patient is a next patient different from the first patient. Certainly, when the same patient is connected to the monitor twice, it may be considered that there are two patients.

In this embodiment, a first method for processing physiological data is described. Specifically, the monitor may automatically clean the physiological data of the first patient at the second time point. Referring to Table 1, Table 1 shows an example of the physiological data of the first patient.

TABLE 1

| Mr. X's physiological data | |
|---|---|
| Heart rate | 75 beats/min |
| Respiration | 18 beats/min |
| Body temperature | 36.2° |
| Blood pressure | Systolic pressure: 100, diastolic pressure: 65 |
| Pulse | 70 beats/min |

At the second time point, Mr. X's physiological data in Table 1 will be cleaned. The data file of the second patient (for example, Ms. Y) is established after clearing. It may be understood that the physiological data of the second patient has not been recorded in the data file yet, that is, as shown in Table 2.

TABLE 2

| Ms. Y's physiological data | |
|---|---|
| Heart rate | / |
| Respiration | / |
| Body temperature | / |
| Blood pressure | Systolic pressure/, diastolic pressure/ |
| Pulse | / |

It should be noted that heart rate, respiration, body temperature, blood pressure, and pulse in Table 1 and Table 2 are only schematics of the physiological data. In an actual case, there may be more or fewer types of physiological data. This is not limited herein.

Again, in this embodiment of the present disclosure, the user may clean the physiological data of the first patient through a simple screen-touching operation. That is, a one-click clean function is implemented. Moreover, the monitor may further automatically establish a data file of a next patient to record subsequent physiological data. In the foregoing manner, data processing efficiency can be improved without repeated manual operations, thereby making the solution more practicable.

A data file of a patient established for the foregoing tables is displayed on a display screen to display or display in real time the physiological data corresponding to the patient. In one of the embodiments, a manner of displaying the physiological data on the display screen may be dividing a display interface of a touch display screen into at least one area, and the at least one area is used for presenting the at least one physiological data of the first patient. Certainly, more than two pieces of physiological data may be combined and displayed together in one area. After the step of executing a patient release operation on the first patient at the second time point, after the second time point, the physiological data of the first patient correspondingly presented in the at least one area is cleaned to wait for the second patient to be connected to the monitor and display the physiological data corresponding to the second patient in real time.

In some embodiments, based on any one of FIG. 1 and the foregoing first to fourth embodiments corresponding to FIG. 1, in a sixth optional embodiment of the method for responding to an operation trajectory provided in the embodiment of the present disclosure, the executing a patient release operation on the first patient at the second time point may comprise:

if the monitor has established a communication connection with a server, sending the physiological data of the first patient to the server at the second time point, wherein the server is configured to store the physiological data corresponding to at least one patient identifier, and different patient identifiers are used to indicate different patients; and if the monitor does not establish a communication connection with the server, storing the physiological data of the first patient at the second time point, and establishing a data file of a second patient, wherein the data file is used to record physiological data of the second patient, and the second patient is a next patient different from the first patient (which may also be referred to as an object). For example, when the first patient is connected to the monitor again, the first patient may be considered as the second patient, or another monitored patient that is connected to the monitor may be considered as the second patient. In this embodiment, a second method for processing physiological data is described. Specifically, the monitor may further establish a communication connection with the server. A connection manner may be a wired manner or a wireless manner. The wireless connection manner comprises, but is not limited to, at least one of Bluetooth communication, Wireless Fidelity (WiFi) communication, and infrared communication. If the monitor has established a communication connection with the server, at the second time point, the monitor may send the physiological data of the first patient to the server. The identifier of the first patient should further be carried when the physiological data of the first patient is sent, to enable the server to confirm the owner of the physiological data according to the identifier.

It may be understood that the server herein may also be referred to as a "central station", is configured to be connected to a plurality of monitors, and has an alarm function. If an abnormality occurs in physiological data of a patient, the server sends an alarm when receiving the physiological data, to implement a function of monitoring the patient's conditions in real time. In addition, the server further provides a function of searching for physiological data of different objects, so that medical personnel can retrieve and analyze the physiological data of the patient in time as required.

If the monitor fails to establish a communication connection with the server, the physiological data of the first patient may be locally stored on the monitor. The monitor also has a storage module configured to store physiological data of at least one patient. In addition, the monitor can further establish a data file of a next object (that is, the second patient) to be tested. The data file is used to record physiological data of the second patient.

Again, in this embodiment of the present disclosure, the user may upload the physiological data of the first patient through a simple screen-touching operation. That is, a one-click upload function is implemented. Moreover, the monitor may further automatically establish a data file of a next object to record subsequent physiological data. In the foregoing manner, data processing efficiency can be improved without repeated manual operations, thereby making the solution more practicable.

In some embodiments, based on any one of FIG. 1 and the foregoing first to fourth embodiments corresponding to FIG. 1, in a seventh optional embodiment of the method for responding to an operation trajectory provided in the embodiment of the present disclosure, the executing a patient release operation on the first patient at the second time point may comprise:

displaying a dialog box at the second time point, wherein the dialog box is used to receive an operation instruction;

if a first operation instruction is received, clearing the physiological data of the first patient according to the first operation instruction; and if a second operation instruction is received, sending the physiological data of the first patient to a server according to the second operation instruction, and clearing the physiological data of the first patient, wherein the server is configured to store the physiological data corresponding to at least one patient identifier, and different patient identifiers are used to indicate different patients.

In this embodiment, a third method for processing physiological data is described. Specifically, in a process of processing the physiological data of the first patient, the dialog box may further be presented on the display interface of the monitor. The dialog box is used to receive an operation instruction triggered by the user.

Figure 6:
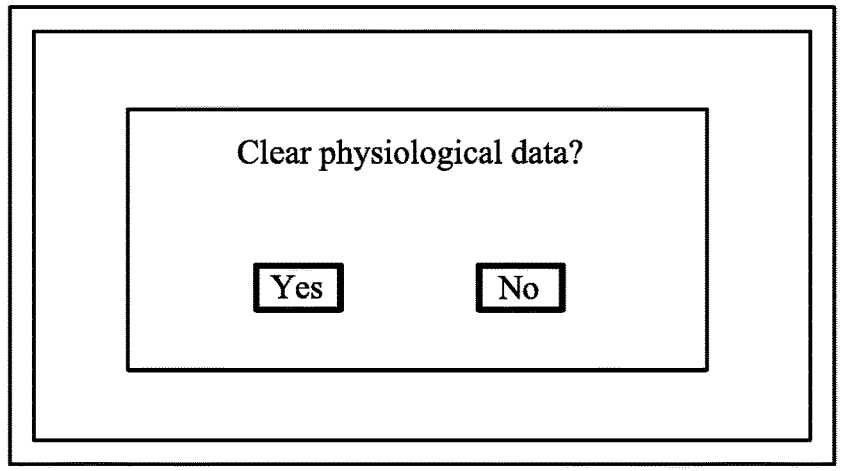
FIG. 6 is a schematic diagram of an interface for inputting a first operation instruction according to embodiments of the present disclosure.

For ease of introduction, referring to FIG. 6, FIG. 6 is a schematic diagram of an interface for inputting a first operation instruction according to embodiments of the present disclosure. As shown in the figure, "Clean physiological data" is displayed in the dialog box. If the user triggers the first operation instruction, that is, selects "Yes", the monitor cleans the physiological data of the first patient according to the first operation instruction.

Figure 7:
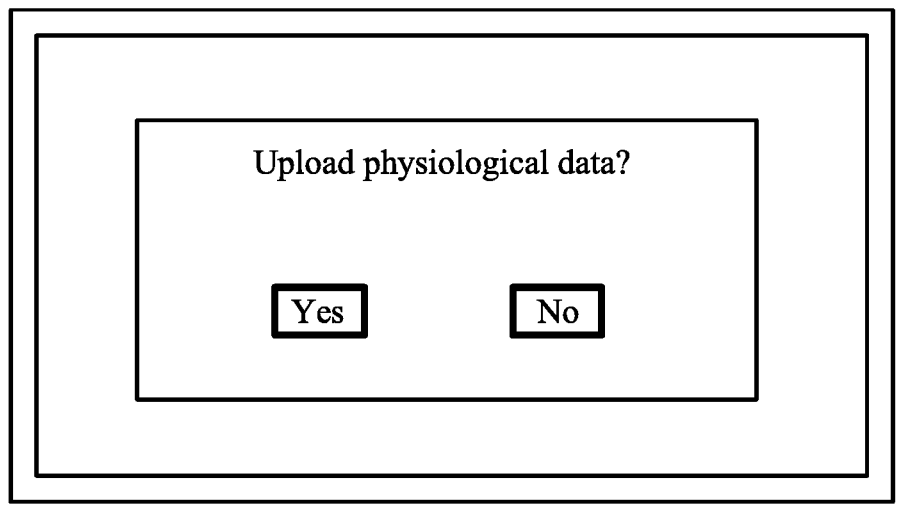
FIG. 7 is a schematic diagram of an interface for inputting a second operation instruction according to embodiments of the present disclosure.

Referring to FIG. 7, FIG. 7 is a schematic diagram of an interface for inputting a second operation instruction according to embodiments of the present disclosure. As shown in the figure, "Upload physiological data" is displayed in the dialog box. If the user triggers the second operation instruction, that is, selects "Yes", the monitor uploads the physiological data of the first patient according to the second operation instruction, and cleans the physiological data of the first patient. In addition, the data file of the second patient is further established.

Again, in this embodiment of the present disclosure, the user may use a simple screen-touching operation as required to confirm a processing manner of the physiological data of the first patient. The processing manner comprises clearing data with one click or uploading and clearing data with one click. In the foregoing manner, data processing efficiency can be improved without repeated manual operations, thereby making the solution more practicable.

As can be seen from the foregoing embodiments, the executing a patient release operation on the first patient at the second time point comprises at least one of the following steps:

popping up a dialog box corresponding to the patient release operation on the display interface, wherein the dialog box corresponding to the patient release operation is used to receive an instruction input for confirming the release of the first patient; and clearing and/or uploading the physiological data of the first patient.

The uploading the physiological data of the first patient may comprise at least one manner of uploading the physiological data of the first patient to a printing output device to print a report, uploading the physiological data of the first patient to a server for storage, etc.

In some embodiments, based on the foregoing seventh embodiment corresponding to FIG. 1, in an eighth optional embodiment of the method for responding to an operation trajectory provided in the embodiment of the present disclosure, before the displaying the dialog box at the second time point, the method may further comprise:

receiving a third operation instruction input by the user through the display interface of the monitor;

determining whether the third operation instruction instructs to display the dialog box on the display interface of the monitor; and if the third operation instruction instructs to display the dialog box on the display interface of the monitor, executing the step of displaying the dialog box at the second time point. The dialog box in this embodiment may be a corresponding dialog box that pops up on the display interface and is configured to input an instruction of the patient release operation.

Figure 8:
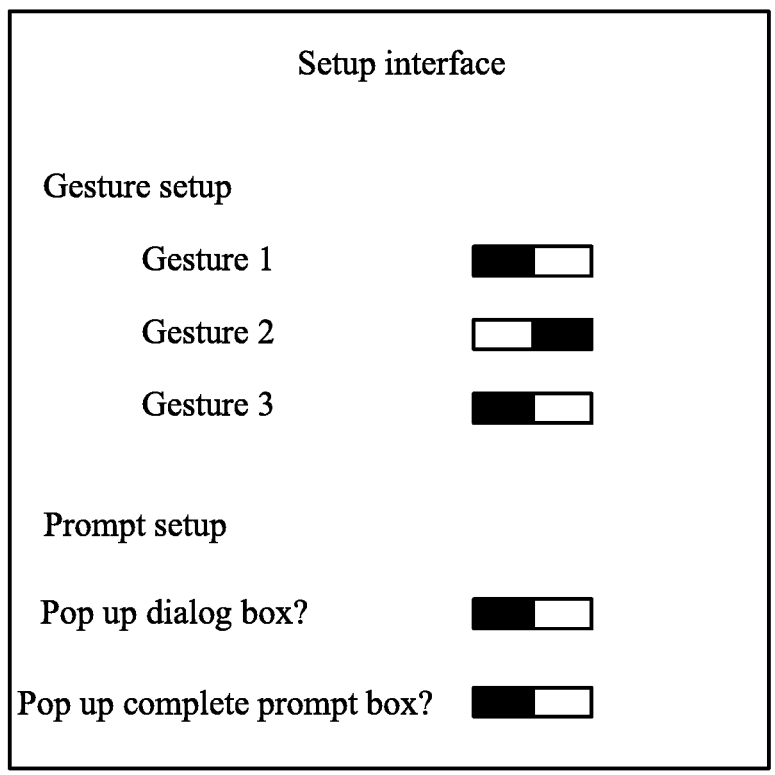
FIG. 8 is a schematic diagram of a user setup interface according to embodiments of the present disclosure.
Figure 9:
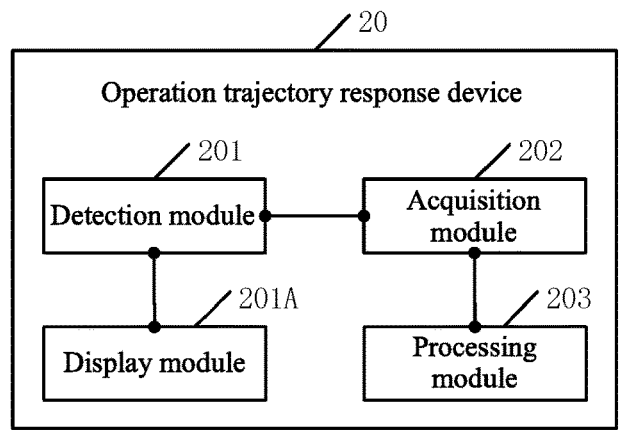
FIG. 9 is a schematic diagram of one embodiment of an operation trajectory response device according to embodiments of the present disclosure.

In this embodiment, the user may pre-set a related parameter on a setup interface. For ease of introduction, referring to FIG. 9, FIG. 9 is a schematic diagram of a user setup interface according to embodiments of the present disclosure. As shown in the figure, the user may input a third operation instruction through the display interface (the setup interface) of the monitor. The monitor determines, according to the third operation instruction, whether the dialog box needs to be displayed. If yes, a dialog box similar to that in FIG. 6, FIG. 7 or FIG. 8 may pop up for selection by the user. Otherwise, if not, a dialog box does not appear.

Similarly, a setup interface may further be set to input another operation instruction, for example, an instruction indicating whether a complete prompt box needs to be popped up. If yes, a prompt "Completed" is displayed after the physiological data of the first patient has been processed.

Further, in this embodiment of the present disclosure, before the monitor displays the dialog box, the third operation instruction input by the user through the display interface of the monitor may further be received. If the third operation instruction instructs to display the dialog box on the display interface of the monitor, the step of displaying the dialog box at the second time point is executed. In the foregoing manner, the user can confirm, according to requirements and use habit, whether to display the dialog box so as to better satisfy the requirements of the user, thereby making the solution more flexible and practicable.

In some embodiments, based on the foregoing embodiment corresponding to FIG. 1, in a ninth optional embodiment of the method for responding to an operation trajectory provided in the embodiment of the present disclosure, before the detecting a screen-touching operation triggered by a user on the current display interface, the method may further comprise:

receiving a fourth operation instruction input by the user through the display interface of the monitor; and
confirming the pre-set operation trajectory according to the fourth operation instruction.

In this embodiment, the user may further set the pre-set operation trajectory on the setup interface. For ease of introduction, referring to FIG. 9 again, FIG. 9 is a schematic diagram of a user setup interface according to embodiments of the present disclosure. As shown in the figure, the user pre-sets a plurality of pre-set operation trajectories. Each pre-set operation trajectory separately corresponds to one name, for example, "Gesture 1". The user may input the fourth operation instruction on the display interface (setup interface) of the monitor. The monitor confirms, according to the fourth operation instruction, which pre-set operation trajectories the user intends to select.

Next, in this embodiment of the present disclosure, before detecting the screen-touching operation triggered by the user on the current display interface, the monitor may further receive a fourth operation instruction input by the user through the display interface of the monitor, and confirm the pre-set operation trajectory according to the fourth operation instruction. In the foregoing manner, the user can customize the pre-set operation trajectory according to requirements and use habit to better satisfy the requirements of the user, thereby making the solution more flexible and practicable.

In addition, in one of the embodiments, after the executing a binding release operation on the first patient, before the establishing a data file of a second patient, or during the clearing the physiological data of the first patient, the method further comprises at least one of the following steps:

1. The display interface of the monitor is switched to a standby interface, or the monitor is controlled to enter a standby state. When the data file of a second object is established discussed herein, an interface used for presenting the physiological data of the second object comprised in the foregoing tables may be displayed on the display interface of the monitor. Certainly, when the second object is not connected to the sensor, corresponding physiological data is empty. Certainly, when the monitor is not connected to a signal input of a sensor, that is, when it indicates that no new patient is connected, it may be considered to use this solution to enable the monitor to enter a standby mode, so that a one-time operation may be used to simply perform one touch control to enable the monitor to enter a standby state, thereby reducing loss. In one of the embodiments, before the interface for presenting the physiological data of the second patient is displayed, the standby interface may be presented first, and the interface for presenting the physiological data of the second patient is entered as soon as the user inputs a corresponding instruction. If the screen for display is a touch display screen, a processor controls the touch display screen to present the standby interface, for example, controls the touch display screen at the second time point to present the standby interface.
2. The physiological data of the first patient is uploaded to a printing output device. For this solution, a one-time operation may be used to simply perform one touch control to enable the monitor to complete the patient release operation and print a corresponding report.
3. The display interface is switched to a corresponding display interface used for displaying the physiological data of the second patient. Regardless of whether there is an input of a sensor signal, one touch control may be used to enable the monitor to complete the patient release operation and directly switch to the interface display of the second patient, so that an operation of switching patients by medical personnel is shortened, and operations of unbinding and binding a patient during transport are omitted.

Figure 10:
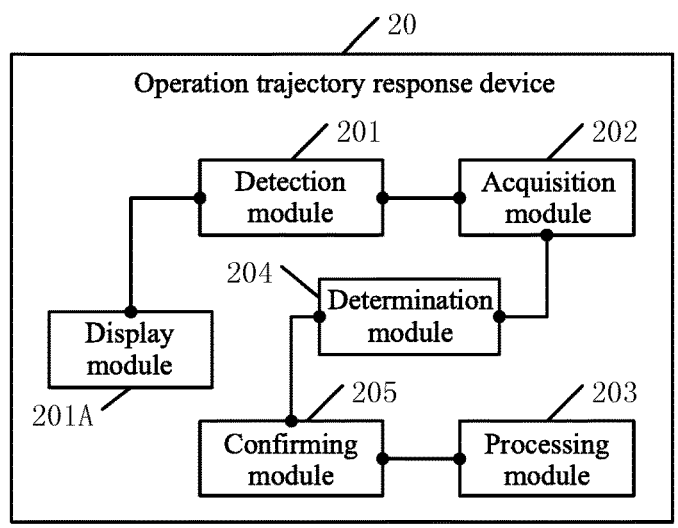
FIG. 10 is a schematic diagram of another embodiment of an operation trajectory response device according to embodiments of the present disclosure.

An operation trajectory response device in the present disclosure is described below in detail. Referring to FIG. 10, the operation trajectory response device according to embodiments of the present disclosure is applied to a monitor. The monitor is configured to monitor physiological data of at least one patient. The operation trajectory response device 20 comprises:

a display module 201A configured to display at least one physiological data of a first patient on a display interface, wherein the at least one physiological data comprises at least one of electrocardiogram, blood oxygen, blood pressure, respiration rate, body temperature and heart rate;
a detection module 201 configured to detect a screen-touching operation triggered by a user on the current display interface;
an acquisition module 202 configured to acquire an operation trajectory corresponding to the screen-touching operation according to the screen-touching operation detected by the detection module 201, wherein the operation trajectory includes a start point and an end point, the start point corresponds to a first time point, the end point corresponds to a second time point, and the second time point is later than the first time point; and
a processing module 203 configured to, if the screen-touching operation acquired by the acquisition module 202 satisfies a pre-set operation trajectory, process the physiological data of the first patient at the second time point.

In this embodiment, the display module 201A displays the at least one physiological data of the first patient on the display interface, wherein the at least one physiological data comprises at least one of electrocardiogram, blood oxygen, blood pressure, respiration rate, body temperature, and heart rate. When the detection module 201 detects the screen-touching operation triggered by the user on the current display interface, the acquisition module 202 acquires the operation trajectory corresponding to the screen-touching operation according to the screen-touching operation detected by the detection module 201. The operation trajectory includes a start point and an end point. The start point corresponds to a first time point, the end point corresponds to a second time point, and the second time point is later than the first time point. If the screen-touching operation acquired by the acquisition module 202 satisfies the pre-set operation trajectory, the processing module 203 executes a patient release operation on the first patient at the second time point.

An embodiment of the present disclosure provides an operation trajectory response device. The device is applied to a monitor. The monitor is configured to monitor physiological data of at least one patient. First, when the monitor monitors physiological data of a first patient, a screen-touching operation triggered by a user on a current display interface is detected. The monitor may then acquire an operation trajectory corresponding to the screen-touching operation according to the screen-touching operation. The operation trajectory includes a start point and an end point. The start point corresponds to a first time point, the end point corresponds to a second time point, and the second time point is later than the first time point. If the operation trajectory satisfies a pre-set operation trajectory, the monitor executes a patient release operation on the first patient at the second time point. In the above manner, on a smaller screen of a monitor, release of physiological data can be completed through an operation trajectory without needing to click on a menu button on a small screen multiple times, which is convenient for a user to operate and improves the ease of use of a monitor.

Figure 11:
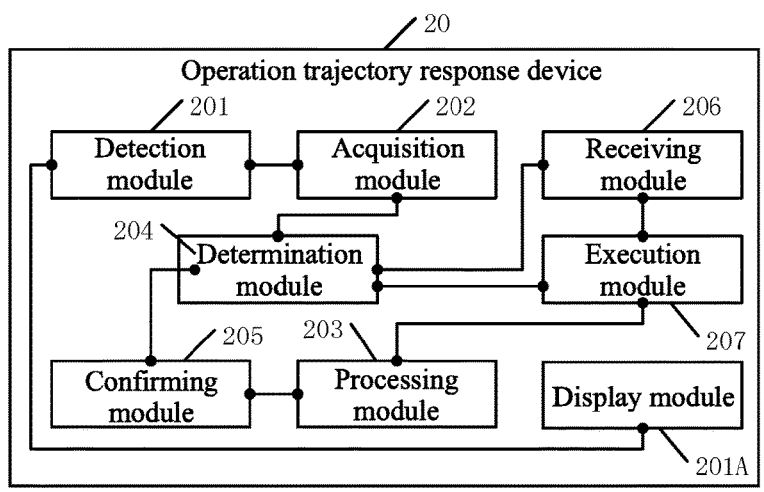
FIG. 11 is a schematic diagram of another embodiment of an operation trajectory response device according to embodiments of the present disclosure.

In some embodiments, based on the foregoing optional embodiment corresponding to FIG. 10, referring to FIG. 11, another embodiment of a trajectory response device 20 provided in the embodiment of the present disclosure further comprises a determination module 204 and a confirming module 205.

The determination module 204 is configured to, after the acquisition module 202 acquires the operation trajectory corresponding to the screen-touching operation according to the screen-touching operation, determine whether the operation trajectory is a swipe trajectory, wherein the direction of the swipe trajectory is at least one of up, down, left, and right.

The confirming module 205 is configured to, if the determination module determines that the obtained operation trajectory is the swipe trajectory, determine that the screen-touching operation satisfies the pre-set operation trajectory.

Next, in this embodiment of the present disclosure, a finger may swipe on the display interface of the monitor to generate one swipe trajectory, and the swipe direction of the swipe trajectory is at least one of up, down, left, and right. In the foregoing manner, the pre-set operation trajectory is set as the swipe trajectory, and the user only needs a simple gesture operation to process the physiological data of the first patient, so that the monitor can be more conveniently used.

In some embodiments, referring to FIG. 11, another embodiment of the trajectory response device 20 provided in the embodiment of the present disclosure further comprises a determination module 204 and a confirming module 205.

The determination module 204 is configured to, after the acquisition module 202 acquires the operation trajectory corresponding to the screen-touching operation according to the screen-touching operation, determine whether the operation trajectory is an arc trajectory, wherein the direction of the arc trajectory is clockwise or counterclockwise.

The confirming module 205 is configured to, if the determination module 204 determines that the obtained operation trajectory is an arc trajectory, confirm that the screen-touching operation satisfies the pre-set operation trajectory.

Next, in this embodiment of the present disclosure, a finger may swipe on the display interface of the monitor to generate one arc trajectory, and the swipe direction of the arc trajectory is clockwise or counterclockwise. In the foregoing manner, the pre-set operation trajectory is set as an arc trajectory. The user only needs to execute a simple gesture operation to execute the patient release operation on the first patient, so that the monitor can be more conveniently used.

In some embodiments, referring to FIG. 11, another embodiment of the trajectory response device 20 provided in the embodiment of the present disclosure further comprises a determination module 204 and a confirming module 205.

The determination module 204 is configured to, after the acquisition module 202 acquires the operation trajectory corresponding to the screen-touching operation according to the screen-touching operation, determine whether the operation trajectory is a pre-set figure, wherein the pre-set figure is a closed figure or a non-closed figure.

The confirming module 205 is configured to, if the determination module 204 determines that the obtained operation trajectory is the pre-set figure, confirm that the screen-touching operation satisfies the pre-set operation trajectory.

Next, in this embodiment of the present disclosure, a finger may swipe on the display interface of the monitor to generate one pre-set figure, and the pre-set figure is a closed figure or a non-closed figure. In the foregoing manner, the pre-set operation trajectory is set as the pre-set figure, and the user only needs to perform a simple gesture operation to process the physiological data of the first patient, so that the monitor can be more conveniently used, and the pre-set operation trajectory is more flexible.

In some embodiments, referring to FIG. 10 or FIG. 11, another embodiment of the trajectory response device 20 provided in the embodiment of the present disclosure comprises:

the processing module 203, configured to, clean the physiological data of the first patient at the second time point; and establish a data file of a second patient, wherein the data file is used to record physiological data of the second patient, and the second patient is a next patient of the first patient.

Again, in this embodiment of the present disclosure, the user may perform a simple screen-touching operation to clean the physiological data of the first patient. That is, a one-click clean function is implemented. Moreover, the monitor may further automatically establish a data file of a next object to record subsequent physiological data. In the foregoing manner, data processing efficiency can be improved without repeated manual operations, thereby making the solution more practicable.

In some embodiments, referring to FIG. 10 or FIG. 11, another embodiment of the trajectory response device 20 provided in the embodiment of the present disclosure comprises:

the processing module 203, configured to, if the monitor has established a communication connection with a server, send the physiological data of the first patient to the server at the second time point, and clean the physiological data of the first patient, wherein the server is configured to store the physiological data corresponding to at least one patient identifier, and different patient identifiers are used to indicate different patients; and if the monitor does not establish a communication connection with the server, store the physiological data of the first patient at the second time point, and establish a data file of a second patient, wherein the data file is used to record physiological data of the second patient, and the second patient is a next patient of the first patient.

Again, in this embodiment of the present disclosure, the user may upload the physiological data of the first patient through a simple screen-touching operation. That is, a one-click upload function is implemented. Moreover, the monitor may further automatically establish a data file of a next object to record subsequent physiological data. In the foregoing manner, data processing efficiency can be improved without repeated manual operations, thereby making the solution more practicable.

In some embodiments, referring to FIG. 10 or FIG. 11, another embodiment of the trajectory response device 20 provided in the embodiment of the present disclosure comprises:

the processing module 203, configured to display a dialog box at the second time point, wherein the dialog box is used to receive an operation instruction;

if a first operation instruction is received, clearing the physiological data of the first patient according to the first operation instruction; and if a second operation instruction is received, send the physiological data of the first patient to a server according to the second operation instruction, and clean the physiological data of the first patient, wherein the server is configured to store the physiological data corresponding to at least one patient identifier, and different patient identifiers are used to indicate different patients.

Again, in this embodiment of the present disclosure, the user may use a simple screen-touching operation as required to confirm a processing manner of the physiological data of the first patient. The processing manner comprises clearing data with one click or uploading and clearing data with one click. In the foregoing manner, data processing efficiency can be improved without repeated manual operations, thereby making the solution more practicable.

Figure 12:
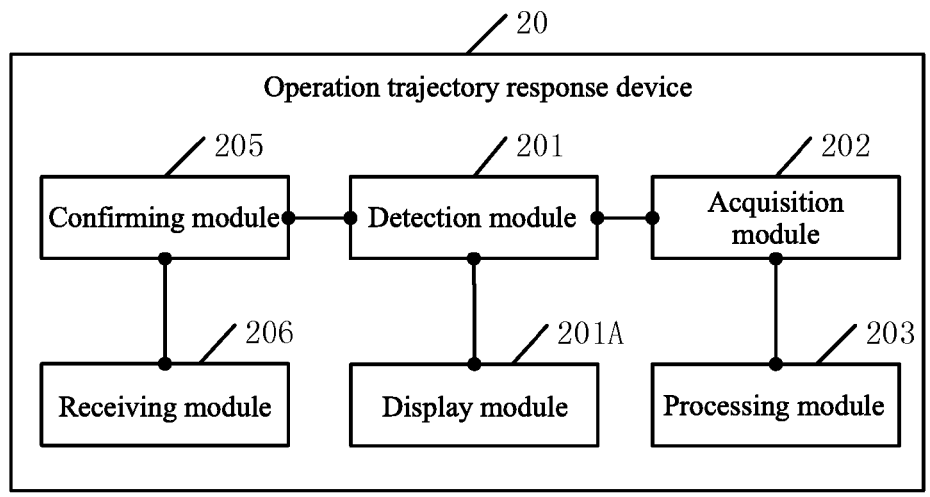
FIG. 12 is a schematic diagram of another embodiment of an operation trajectory response device according to embodiments of the present disclosure.

In some embodiments, based on the foregoing optional embodiment corresponding to FIG. 10 or FIG. 11, referring to FIG. 12, another embodiment of the trajectory response device 20 provided in the embodiment of the present disclosure further comprises a receiving module 206 and an execution module 207.

The receiving module 206 is configured to, before the processing module 203 displays the dialog box at the second time point, receive a third operation instruction input by the user through the display interface of the monitor.

The determination module 204 is further configured to determine whether the third operation instruction received by the receiving module 206 instructs to display the dialog box on the display interface of the monitor.

The execution module 207 is configured to, if the determination module 204 determines that the obtained third operation instruction instructs to display the dialog box on the display interface of the monitor, perform the step of displaying the dialog box at the second time point.

Further, in this embodiment of the present disclosure, before the monitor displays the dialog box, the third operation instruction input by the user through the display interface of the monitor may further be received. If the third operation instruction instructs to display the dialog box on the display interface of the monitor, the step of displaying the dialog box at the second time point is executed. In the foregoing manner, the user can confirm, according to requirements and use habit, whether to display the dialog box so as to better satisfy the requirements of the user, thereby making the solution more flexible and practicable.

Figure 13:
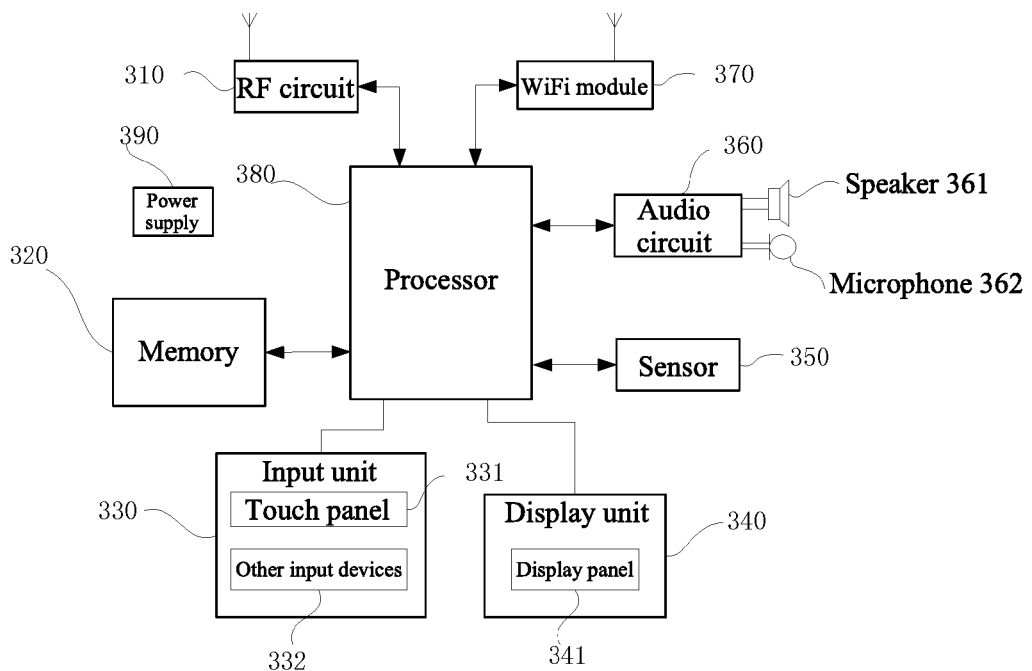
FIG. 13 is a schematic structural diagram of an operation trajectory response device according to embodiments of the present disclosure.

In some embodiments, based on the foregoing optional embodiment corresponding to FIG. 10, referring to FIG. 13, another embodiment of the trajectory response device 20 provided in the embodiment of the present disclosure further comprises a receiving module 206 and a confirming module 205.

The receiving module 206 is further configured to, before the detection module 201 detects the screen-touching operation triggered by the user on the current display interface, receive a fourth operation instruction input by the user through the display interface of the monitor.

The confirming module 205 is further configured to confirm the pre-set operation trajectory according to the fourth operation instruction received by the receiving module 206.

Next, in this embodiment of the present disclosure, before detecting the screen-touching operation triggered by the user on the current display interface, the monitor may further receive a fourth operation instruction input by the user through the display interface of the monitor, and confirm the pre-set operation trajectory according to the fourth operation instruction. In the foregoing manner, the user can customize the pre-set operation trajectory according to requirements and use habit to better satisfy the requirements of the user, thereby making the solution more flexible and practicable.

An embodiment of the present disclosure further provides another monitor. As shown in FIG. 13, for ease of description, only parts related to the embodiment of the present disclosure are shown. For specific technical details that are not disclosed, refer to the method part of the embodiments of in the present disclosure. FIG. 13 is a block diagram of a partial structure related to the monitor provided in the embodiment of the present disclosure. Referring to FIG. 13, the monitor may comprise components such as a radio frequency (RF) circuit 310, a memory 320, an input unit 330, a display unit 340, a sensor 350, an audio circuit 360, a wireless fidelity (WiFi) module 370, a processor 380, and a power supply 390. A person skilled in the art may understand that the structure of the monitor shown in FIG. 13 does not constitute a limitation to the monitor. More or fewer components may be comprised, some components are combined, or components are differently arranged.

The components of the monitor are described below in detail with reference to FIG. 13.

The RF circuit 310 may be configured to receive and transmit signals in a process of receiving and transmitting information or communication. Generally, the RF circuit 310 comprises, but is not limited to, an antenna, at least one amplifier, a transceiver, a coupler, a low noise amplifier (LNA), a duplexer, etc. In addition, the RF circuit 310 may also communicate with a network and other devices by wireless communication. The above wireless communication may use any communication standard or protocol, which comprises, but is not limited to, global system for mobile communications (GSM), general packet radio service (GPRS), code division multiple access (CDMA), wideband code division multiple access (WCDMA), long term evolution (LTE), E-mail, short messaging service (SMS), etc.

The memory 320 may be configured to store software programs and modules, and the processor 380 executes various functional applications and data processing of the monitor by running the software programs and the modules stored in the memory 320. The memory 320 may mainly comprise a program storage area and a data storage area. The storage program area may store an operating system, application programs for at least one function (for example, a sound playback function, and an image display function), etc. The data storage area may store data (for example, audio data, and a phone book) created according to the use of a monitor. In addition, the memory 320 may comprise a high-speed random access memory (RAM), and may further comprise a non-volatile memory such as at least one disk storage device, a flash device or another volatile solid-state storage device.

The input unit 330 may be configured to receive input digital or character information and generate key signal input associated with user setup and functional control of the monitor. Specifically, the input unit 330 may comprise a touch panel 331 and another input device 332. The touch panel 331, also referred to as a touch screen, may acquire a screen-touching operation of a user thereon or nearby (for example, an operation on a touch panel 331 or near the touch panel 331 by the user using a finger, a stylus or any suitable object or accessory), and drive a corresponding connection device according to a pre-set program. In some embodiments, the touch panel 331 may comprise a touch detection device and a touch controller. The touch detection device detects the touching position of the user and detects a signal resulted from the screen-touching operation, and transmits the signal to the touch controller. The touch controller receives the touch information from the touch detection device and converts the information into contact coordinates and sends it to the processor 380, and the touch controller can receive and execute the command sent by the processor 380. In addition, the touch panel 331 can be implemented using various types such as a resistive type, a capacitive type, an infrared type, and a surface acoustic wave type. In addition to the touch panel 331, the input unit 330 may also comprise other input devices 332. Specifically, the other input devices 332 may comprise, but are not limited to, one or more of a physical keyboard, a functional key (for example, volume control buttons, and switch buttons), a trackball, a mouse, and a joystick.

The display unit 340 may be configured to display information input by the user or information provided to the user and various menus of the monitor. The display unit 340 may comprise a display panel 341, and in some embodiments, the display panel 341 may be configured in the form of a liquid crystal display (LCD), an organic light-emitting diode (OLED), etc. Further, the touch panel 331 may cover the display panel 341. When the touch panel 331 detects a screen-touching operation thereon or nearby the display panel, information of the screen-touching operation can be transmitted to the processor 380 to confirm the type of the touch event. The processor 380 then provides a corresponding visual output on the display panel 341 according to the type of the touch event. Although in FIG. 13, the touch panel 331 and the display panel 341 are used as two separate components to implement the input and output functions of the monitor. However, in some embodiments, the touch panel 331 may be integrated with the display panel 341 to implement the input and output functions of the monitor.

The monitor may further comprise at least one physiological data monitoring module configured to monitor physiological data of at least one patient. The physiological data monitoring module comprises: one or a combination of a plurality of an electrocardiographic monitoring module configured to monitor an electrocardiographic signal in real time, a blood oxygen monitoring module configured to monitor a blood oxygen signal in real time, a carbon dioxide monitoring module configured to monitor a breathed gas in real time, a respiration monitoring module configured to monitor respiration in real time (for example, breathing resistance is used to monitor respiration), a temperature monitoring module configured to monitor body temperature in real time, a blood pressure monitoring module configured to monitor a blood pressure signal in real time, etc. Certainly, each type of physiological monitoring module needs to cooperate with a corresponding sensor to acquire source data. For example, the blood oxygen monitoring module requires data input by a blood oxygen probe, the electrocardiographic monitoring module requires an input from an electrode monitoring signal, etc. Therefore, for a monitor, a plurality of monitoring probes or sensors may further be comprised. Certainly, these monitoring probes or sensors may be fixedly connected to the monitor or may be connected to the monitor in a pluggable manner through an interface module. Still further, the at least one physiological data monitoring module may use a detachable board design or may use an integrated board design. Therefore, the at least one physiological data monitoring module may be integrated on one or more processor motherboard or may share one processor motherboard with a processor.

In addition, the monitor may further comprise at least one sensor 350 such as a light sensor, a motion sensor, and other sensors. Specifically, the light sensor may include an ambient light sensor and a proximity sensor, among which the ambient light sensor may adjust the brightness of the display panel 341 according to ambient light, and the proximity sensor may turn off the display panel 341 and/or backlight when the monitor is moved near the ear. As a kind of motion sensor, the accelerometer sensor can detect the magnitude of acceleration in all directions (typically three axes). The accelerometer sensor can detect the magnitude and direction of gravity when stationary. The accelerometer sensor can also identify the application of monitor gestures (such as switching between landscape and portrait screens, related games, magnetometer attitude calibration), or the accelerometer sensor can be used for vibration recognition related functions (such as a pedometer, percussion), etc. The monitor can also be equipped with a gyroscope, a barometer, a hygrometer, a thermometer, an infrared sensor, among other sensors. Details are not described herein.

The audio circuit 360, the speaker 361, the microphone 362 may provide an audio interface between the user and the monitor. The audio circuit 360 may convert the received audio data into electrical data and transfer the electrical data to the speaker 361. The speaker 361 converts the electrical data into a sound signal for output. On the other hand, the microphone 362 converts the acquired sound signal into an electrical signal which will be received by the audio circuit 360 and converted into audio data for output to the processor 380. The audio data is then processed by the processor and transmitted via an RF circuit 310 to, for example, another monitor, or, the audio data is output to the memory 320 for further processing.

WiFi belongs to a short-range wireless transmission technology. The monitor may assist the user in E-mail receiving and sending, webpage browsing, access to streaming media, etc. by means of the WiFi module 370. WiFi provides users with wireless broadband Internet access. Although illustrated in FIG. 13, it should be understood that the WiFi module 370 is not a necessary part of the monitor and can be omitted according to actual needs without departing from the essential nature of the present disclosure.

The processor 380 is the control center of the monitor, and it uses various interfaces and lines to connect to various parts of the whole monitor, runs or executes software programs and/or modules stored in the memory 320, and calls data stored in the memory 320 to perform various functions of the monitor and process data, thereby performing overall monitoring of the monitor. In some embodiments, the processor 380 may include one or more processing units. In some embodiments, the processor 380 may integrate an application processor and a modem processor. The application processor mainly handles the operating system, the user interface, the application, etc. The modem processor mainly processes wireless communication. It will be appreciated that the above-mentioned modem processor may not be integrated into the processor 380.

The monitor further includes a power supply 390 (for example, a battery) that supplies power to various components. In some embodiments, the power supply may be logically connected to the processor 380 via a power management system to enable management of charging, discharging, and power consumption through the power management system.

Although not illustrated, the monitor may include a camera, a Bluetooth module, etc., and will not be elaborated here.

The monitor further includes a bus system. The bus system is configured to be connected to the memory, the transceiver, the at least one physiological data monitoring module, and the processor, so that the memory, the transceiver, and the processor performs communication. The transceiver described herein may include a communication module such as a WiFi module 370 or an RF module 310.

In this embodiment of the present disclosure, the processor 380 comprised in the terminal further has the following functions:

detecting a screen-touching operation triggered by a user on a current display interface;

acquiring an operation trajectory corresponding to the above screen-touching operation according to the above screen-touching operation, wherein the above operation trajectory includes a start point and an end point, the above start point corresponds to a first time point, the above end point corresponds to a second time point, and the above second time point is later than the first time point; and if the screen-touching operation satisfies a pre-set operation trajectory, executing a patient release operation on a first patient at the second time point.

For the foregoing functions or additional functions provided by the processor 380, reference may be made to the detailed description of the method steps in the foregoing embodiments.

In the above embodiments, the disclosed systems and methods may be implemented in whole or in part by software, hardware, firmware, or any combination thereof. When implemented with software, it may be implemented in whole or in part in the form of a computer program product.

The computer program product comprises one or more computer instructions. When the instructions of the computer program are loaded and executed on a computer, the processes or functions according to the embodiments of the present disclosure are generated in whole or in part. The computer may be a general-purpose computer, a special-purpose computer, a computer network, or other programmable devices. The computer instructions may be stored in a computer-readable storage medium or transferred from one computer-readable storage medium to another computer-readable storage medium. For example, the computer instruction may be transmitted from one website, computer, server or data center to another web site, computer, server or data center in a wired manner (for example, a coaxial cable, an optical fiber or a digital subscriber line (DSL)) or a wireless manner (for example, infrared, radio or microwave). The computer readable storage medium may be any available medium that a computer can store data with or a data storage device such as a server, a data center, or the like that comprises one or more integrated available media. The available medium may be a magnetic medium (for example, a floppy disk, a hard disk, and a magnetic tape), an optical medium (for example, a digital versatile disc (DVD)) or a semiconductor medium (for example, a solid-state disk (SSD)).

Those skilled in the art would have clearly understood that for convenience and conciseness of description, the specific working processes of the above-described systems, devices and units can refer to the corresponding processes in the above-described embodiments of the method and will not be further described here.

In several embodiments provided in the present disclosure, it is to be understood that the disclosed systems, devices and methods may be implemented in other ways. For example, the apparatus embodiments described above are merely exemplary. For example, the division of the units is only a logic function division. In actual implementation, there may be other division methods, for example, multiple units or assemblies may be combined or integrated into another system, or some features may be omitted or not implemented. In a further aspect, the mutual coupling or direct coupling or communication connection shown or discussed may be indirect coupling or communication connection through some interfaces, devices or units, and may be in electrical, mechanical or other forms.

The units described as separate parts may or may not be physically separated, and the parts displayed as units may or may not be physical units, i.e., may be located in one place or may be distributed over multiple network units. Some or all of the units can be selected according to actual needs to achieve the purpose of the present embodiment.

In addition, the functional units in the embodiments of the present disclosure may be integrated into one processing unit or may alternatively exist as being physically separate, or two or more of the units may be integrated into one unit. The above integrated unit can be implemented in the form of hardware or a software function unit.

If the integrated unit is implemented in the form of a software function unit and sold or used as an independent product, it may be stored in a computer-readable storage medium. Based on such an understanding, the technical solutions of the present disclosure essentially, or the part contributing to the prior art may be implemented in the form of a software product. The computer software product may be stored in a storage medium and includes several instructions for instructing a computer device (which may be a personal computer, a server, or a network device) to perform all or some of the steps of the methods described in the embodiments of the present disclosure. The aforementioned storage medium comprises: any medium that can store program code, such as a Universal Serial Bus (USB) flash drive, a removable hard disk, a read-only memory (ROM), a RAM, a magnetic disk or an optical disc.

As described above, the above embodiments are only for the purpose of illustration of the technical solution of the present disclosure and not limitation; and although the present disclosure has been described in detail with reference to the foregoing embodiments, it should be understood by those of ordinary skill in the art that modifications can still be made to the technical solution described in the foregoing embodiments or equivalent substitutions of some technical features thereof is also possible, while these modifications or substitutions do not make the essence of the corresponding technical solution depart from the spirit and scope of the technical solutions of the embodiments of the present disclosure.

What is claimed is:

1. A method for responding to an operation trajectory, the method being applied to a monitor configured to monitor and display physiological data of a patient, the method comprising:

displaying at least one physiological data of a first patient on a display interface, wherein the monitor is bound to the first patient and the at least one physiological data is obtained exclusively from the first patient, wherein the at least one physiological data comprises at least one of electrocardiogram, blood oxygen, blood pressure, respiration rate, body temperature or heart rate;

detecting a screen-touching operation triggered by a user on the display interface;

acquiring an operation trajectory corresponding to the screen-touching operation according to the screen-touching operation, wherein the operation trajectory comprises a start point and an end point, the start point corresponding to a first time point, the end point corresponding to a second time point, and the second time point being later than the first time point; and if the screen-touching operation satisfies a pre-set operation trajectory, executing a patient release operation to release a binding relationship between the monitor and the first patient at the second time point, such that the monitor no longer monitors any physiological data of the first patient.

2. The method of claim 1, wherein after the operation of acquiring an operation trajectory corresponding to the screen-touching operation according to the screen-touching operation, the method further comprises:

determining whether the operation trajectory is a swipe trajectory, wherein a direction of the swipe trajectory is at least one of up, down, left and right; and if the operation trajectory is the swipe trajectory, confirming that the screen-touching operation satisfies the pre-set operation trajectory.

3. The method of claim 1, wherein after the operation of acquiring an operation trajectory corresponding to the screen-touching operation according to the screen-touching operation, the method further comprises:

determining whether the operation trajectory is an arc trajectory, wherein a direction of the arc trajectory is a clockwise direction or a counterclockwise direction; and if the operation trajectory is an arc trajectory, confirming that the screen-touching operation satisfies the pre-set operation trajectory.

4. The method of claim 1, wherein after the operation of acquiring an operation trajectory corresponding to the screen-touching operation according to the screen-touching operation, the method further comprises:

determining whether the operation trajectory is a pre-set figure, wherein the pre-set figure is a closed figure or a non-closed figure; and if the operation trajectory is the pre-set figure, confirming that the screen-touching operation satisfies the pre-set operation trajectory.

5. The method of claim 1, wherein the screen-touching operation is triggered by one finger, or is triggered by two fingers, or is triggered by more than two fingers.

6. The method of claim 1, wherein the operation of executing a patient release operation to release a binding relationship between the monitor and the first patient at the second time point comprises at least one of the following steps:

popping up a dialog box corresponding to the patient release operation on the display interface, wherein the dialog box corresponding to the patient release operation is used to receive an instruction input for confirming the release of the first patient; and clearing and uploading the physiological data of the first patient.

7. The method of claim 1, wherein the operation of executing a patient release operation to release a binding relationship between the monitor and the first patient at the second time point comprises:

clearing the physiological data of the first patient at the second time point; and establishing a data file of a second patient, wherein the data file is used to record physiological data of the second patient.

8. The method of claim 1, wherein after executing a patient release operation to release a binding relationship between the monitor and the first patient at the second time point, before establishing a data file of a second patient or when clearing the physiological data of the first patient, the method further comprises at least one of the following steps:

switching the display interface to a standby interface;

controlling the monitor to enter a standby state;

uploading the physiological data of the first patient to a printing output device; and switching the display interface to a corresponding display interface used for displaying physiological data of the second patient.

9. The method of claim 1, wherein before the step of detecting a screen-touching operation triggered by a user on the display interface, the method further comprises:

receiving an operation instruction input by the user through the display interface of the monitor; and confirming the pre-set operation trajectory according to the operation instruction.

10. A method for responding to an operation trajectory, the method being applied to a monitor configured to monitor and display physiological data of a patient, the method comprising:

displaying at least one physiological data of a first patient on a display interface, wherein the at least one physiological data comprises at least one of electrocardiogram, blood oxygen, blood pressure, respiration rate, body temperature or heart rate;

detecting a screen-touching operation triggered by a user on the display interface;

acquiring an operation trajectory corresponding to the screen-touching operation according to the screen-touching operation, wherein the operation trajectory comprises a start point and an end point, the start point corresponding to a first time point, the end point corresponding to a second time point, and the second time point being later than the first time point; and if the screen-touching operation satisfies a pre-set operation trajectory, executing a patient release operation on the first patient at the second time point, wherein the operation of executing a patient release operation on the first patient at the second time point comprises:

if the monitor has established a communication connection with a server, sending the physiological data of the first patient to the server at the second time point, and clearing the physiological data of the first patient, wherein the server is configured to store the physiological data corresponding to at least one patient identifier, and different patient identifiers are used to indicate different objects; and if the monitor has not established a communication connection with the server, storing the physiological data of the first patient at the second time point, and establishing a data file of a second patient, wherein the data file is used to record physiological data of the second patient.

11. A method for responding to an operation trajectory, the method being applied to a monitor configured to monitor and display physiological data of a patient, the method comprising:
displaying at least one physiological data of a first patient on a display interface, wherein the at least one physiological data comprises at least one of electrocardiogram, blood oxygen, blood pressure, respiration rate, body temperature or heart rate;
detecting a screen-touching operation triggered by a user on the display interface;
acquiring an operation trajectory corresponding to the screen-touching operation according to the screen-touching operation, wherein the operation trajectory comprises a start point and an end point, the start point corresponding to a first time point, the end point corresponding to a second time point, and the second time point being later than the first time point; and
if the screen-touching operation satisfies a pre-set operation trajectory, executing a patient release operation on the first patient at the second time point, wherein the operation of executing a patient release operation on the first patient at the second time point comprises:
displaying a dialog box at the second time point, wherein the dialog box is used to receive an operation instruction;
if a first operation instruction is received, clearing the physiological data of the first patient according to the first operation instruction; and
if a second operation instruction is received, sending the physiological data of the first patient to a server according to the second operation instruction, clearing the physiological data of the first patient, and establishing a data file of a second patient.

12. The method of claim 11, wherein before the operation of displaying the dialog box at the second time point, the method further comprises:
receiving a third operation instruction input by the user through the display interface of the monitor;
determining whether the third operation instruction instructs to display the dialog box on the display interface of the monitor; and
if the third operation instruction instructs to display the dialog box on the display interface of the monitor, performing the step of displaying the dialog box at the second time point.

13. An operation trajectory response device, the operation trajectory response device being applied to a monitor configured to monitor and display physiological data of a patient, the operation trajectory response device comprising:
a display module configured to display at least one physiological data of a first patient on a display interface, wherein the monitor is bound to the first patient and the at least one physiological data is obtained exclusively from the first patient, wherein the at least one physiological data comprises at least one of electrocardiogram, blood oxygen, blood pressure, respiration rate, body temperature or heart rate;
a detection module configured to detect a screen-touching operation triggered by a user on the display interface;
an acquisition module configured to acquire an operation trajectory corresponding to the screen-touching operation according to the screen-touching operation detected by the detection module, wherein the operation trajectory includes a start point and an end point, the start point corresponds to a first time point, the end point corresponds to a second time point, and the second time point is later than the first time point; and
a processing module configured to, if the screen-touching operation acquired by the acquisition module satisfies a pre-set operation trajectory, execute a patient release operation to release a binding relationship between the monitor and the first patient at the second time point, such that the monitor no longer monitors any physiological data of the first patient.

14. A monitor, comprising:
a touch display screen;
a processor; and
a memory, at least one physiological data monitoring module and a bus system, wherein the at least one physiological data monitoring module is configured to monitor at least one physiological data of a patient;
the memory is configured to store a program, an instruction, and the at least one physiological data of the patient;
the touch display screen receives a screen-touching operation under the control of the processor;
the processor is configured to execute the program in the memory;
the bus system is configured to be connected to the memory, the at least one physiological data monitoring module and the processor to enable the memory and the processor to perform communication; and
the processor is configured to further perform the following steps:
displaying at least one physiological data of a first patient on a display interface of the touch display screen, wherein the monitor is bound to the first patient and the at least one physiological data is obtained exclusively from the first patient, wherein the at least one physiological data comprises at least one of electrocardiogram, blood oxygen, blood pressure, respiration rate, body temperature or heart rate;
detecting the screen-touching operation triggered by a user on the display interface;
acquiring an operation trajectory corresponding to the screen-touching operation according to the screen-touching operation, wherein the operation trajectory includes a start point and an end point, the start point corresponds to a first time point, the end point corresponds to a second time point, and the second time point is later than the first time point; and
if the screen-touching operation satisfies a pre-set operation trajectory, executing a patient release operation to release a binding relationship between the monitor and the first patient at the second time point, such that the monitor no longer monitors any physiological data of the first patient.

15. The monitor of claim 14, wherein the processor is further configured to perform the following steps:
determining whether the operation trajectory is a swipe trajectory, wherein a direction of the swipe trajectory is at least one of up, down, left and right; and if the operation trajectory is the swipe trajectory, confirming that the screen-touching operation satisfies the pre-set operation trajectory, or
determining whether the operation trajectory is an arc trajectory, wherein the direction of the arc trajectory is a clockwise direction or a counterclockwise direction; and if the operation trajectory is an arc trajectory, confirming that the screen-touching operation satisfies the pre-set operation trajectory; or determining whether the operation trajectory is a pre-set figure, wherein the pre-set figure is a closed figure or a non-closed figure; and if the operation trajectory is the pre-set figure, confirming that the screen-touching operation satisfies the pre-set operation trajectory.

16. The monitor of claim 14, wherein the processor is further configured to perform at least one of the following steps:

popping up a dialog box corresponding to the patient release operation on the display interface, wherein the dialog box corresponding to the patient release operation is used to receive an instruction input for confirming the release of the first patient; and clearing and/or uploading the physiological data of the first patient.

17. The monitor of claim 14, wherein the processor is configured to perform the following steps:

clearing the physiological data of the first patient at the second time point; and establishing a data file of a second patient, wherein the data file is used to record physiological data of the second patient.

18. The monitor of claim 14, wherein the processor is configured to, after executing the patient release operation to release a binding relationship between the monitor and the first patient at the second time point; before establishing a data file of a second patient, or when clearing the physiological data of the first patient, further perform at least one of the following steps:

controlling the monitor to enter a standby state;

controlling the touch display screen to present a standby interface;

uploading the physiological data of the first patient to a printing output device; and switching the display interface to a corresponding display interface used for displaying physiological data of the second patient.

19. The monitor of claim 14, wherein the processor further performs the following steps:

receiving an operation instruction input by the user through the display interface of the monitor; and confirming the pre-set operation trajectory according to the operation instruction.

20. The monitor of claim 14, wherein the processor implements the displaying the at least one physiological data of the first patient on the display, interface by means of the following manner:

dividing the display interface of the touch display screen into at least one area, wherein the at least one area is used for presenting the at least one physiological data of the first patient; and the processor implements the executing the patient release operation to release a binding relationship between the monitor and the first patient at the second time point by means of the following manner:

after the second time point, clearing the physiological data of the first patient correspondingly presented on the at least one area.

21. A monitor, comprising:

a touch display screen;

a processor; and a memory, at least one physiological data monitoring module and a bus system, wherein the at least one physiological data monitoring module is configured to monitor at least one physiological data of a patient;

the memory is configured to store a program, an instruction, and the at least one physiological data of the patient;

the touch display screen receives a screen-touching operation under the control of the processor;

the processor is configured to execute the program in the memory;

the bus system is configured to be connected to the memory, the at least one physiological data monitoring module and the processor to enable the memory and the processor to perform communication; and the processor is configured to further perform the following steps:

displaying at least one physiological data of a first patient on a display interface of the touch display screen, wherein the at least one physiological data comprises at least one of electrocardiogram, blood oxygen, blood pressure, respiration rate, body temperature or heart rate;

detecting the screen-touching operation triggered by a user on the display interface;

acquiring an operation trajectory corresponding to the screen-touching operation according to the screen-touching operation, wherein the operation trajectory includes a start point and an end point, the start point corresponds to a first time point, the end point corresponds to a second time point, and the second time point is later than the first time point;

if the screen-touching operation satisfies a pre-set operation trajectory, executing a patient release operation on the first patient at the second time point;

if the monitor has established a communication connection with a server, sending the physiological data of the first patient to the server at the second time point, and clearing the physiological data of the first patient, wherein the server is configured to store the physiological data corresponding to at least one patient identifier, and different patient identifiers are used to indicate different objects; and if the monitor has not established a communication connection with the server, storing the physiological data of the first patient at the second time point, and establishing a data file of a second patient, wherein the data file is used to record physiological data of the second patient, and the second patient is a next object of the first patient.

22. A monitor, comprising:

a touch display screen;

a processor; and a memory, at least one physiological data monitoring module and a bus system, wherein the at least one physiological data monitoring module is configured to monitor at least one physiological data of a patient;

the memory is configured to store a program, an instruction, and the at least one physiological data of the patient;

the touch display screen receives a screen-touching operation under the control of the processor;

the processor is configured to execute the program in the memory;

the bus system is configured to be connected to the memory, the at least one physiological data monitoring module and the processor to enable the memory and the processor to perform communication; and the processor is configured to further perform the following steps:

displaying at least one physiological data of a first patient on a display interface of the touch display screen, wherein the at least one physiological data comprises at least one of electrocardiogram, blood oxygen, blood pressure, respiration rate, body temperature or heart rate;

detecting the screen-touching operation triggered by a user on the display interface;

acquiring an operation trajectory corresponding to the screen-touching operation according to the screen-touching operation, wherein the operation trajectory includes a start point and an end point, the start point corresponds to a first time point, the end point corresponds to a second time point, and the second time point is later than the first time point;

if the screen-touching operation satisfies a pre-set operation trajectory, executing a patient release operation on the first patient at the second time point;

displaying a dialog box at the second time point, wherein the dialog box is used to receive an operation instruction;

if a first operation instruction is received, clearing the physiological data of the first patient according to the first operation instruction; and if a second operation instruction is received, sending the physiological data of the first patient to a server according to the second operation instruction, and clearing the physiological data of the first patient.

23. The monitor of claim 22, wherein the processor further performs the following steps:

receiving a third operation instruction input by the user through the display interface of the monitor;

determining whether the third operation instruction instructs to display the dialog box on the display interface of the monitor; and if the third operation instruction instructs to display the dialog box on the display interface of the monitor, performing the step of displaying the dialog box at the second time point.

* * * * *